United States Patent
Rytky

(10) Patent No.: US 7,171,259 B2
(45) Date of Patent: Jan. 30, 2007

(54) METHOD AND DEVICE FOR MEASURING HEART RATE, AND METHOD FOR MANUFACTURING THE DEVICE

(75) Inventor: Pekka Rytky, Oulu (FI)

(73) Assignee: Polar Electro Oy, Kempele (FI)

( * ) Notice: Subject to any disclaimer, the term of this patent is extended or adjusted under 35 U.S.C. 154(b) by 97 days.

(21) Appl. No.: 10/825,857

(22) Filed: Apr. 16, 2004

(65) Prior Publication Data

US 2004/0220485 A1 Nov. 4, 2004

(30) Foreign Application Priority Data

Apr. 17, 2003 (FI) .................................. 20030598

(51) Int. Cl.
*A61B 5/04* (2006.01)
(52) U.S. Cl. ....................................................... 600/509
(58) Field of Classification Search ................ 600/509, 600/519, 522
See application file for complete search history.

(56) References Cited

U.S. PATENT DOCUMENTS

| 3,826,246 | A | * | 7/1974 | Raddi et al. ................. 600/382 |
| 3,870,034 | A | * | 3/1975 | James ........................ 600/547 |
| 4,091,610 | A | * | 5/1978 | Sasaki et al. ................ 368/187 |
| 4,120,294 | A | * | 10/1978 | Wolfe ........................ 600/519 |
| 4,230,127 | A | | 10/1980 | Larson ....................... 128/706 |
| 4,248,244 | A | | 2/1981 | Charnitski et al. .......... 128/706 |
| 4,295,472 | A | * | 10/1981 | Adams ....................... 600/503 |
| 4,407,295 | A | * | 10/1983 | Steuer et al. ............... 600/483 |
| 4,938,228 | A | * | 7/1990 | Righter et al. .............. 600/503 |
| 5,526,006 | A | | 6/1996 | Akahane et al. ............ 348/718 |
| 5,738,104 | A | * | 4/1998 | Lo et al. ..................... 600/521 |
| 5,810,736 | A | * | 9/1998 | Pail .......................... 600/500 |
| 5,894,454 | A | * | 4/1999 | Kondo ........................ 368/11 |
| 6,491,647 | B1 | | 12/2002 | Bridger et al. .............. 600/585 |
| 6,950,695 | B2 | * | 9/2005 | Chen ......................... 600/509 |

FOREIGN PATENT DOCUMENTS

| EP | 0540154 A1 | 5/1993 |
| EP | 1034736 A1 | 9/2000 |

* cited by examiner

*Primary Examiner*—Robert E. Pezzuto
*Assistant Examiner*—Brian T. Gedeon
(74) *Attorney, Agent, or Firm*—Hoffmann & Baron, LLP

(57) ABSTRACT

A heart rate measuring device is attached around a user's hand, the device having an inner surface, which is in contact with the skin on the hand to which it is attached, and an outer surface, which is other than the inner surface. The inner surface of the measuring device is provided with an electrically conductive inner structure, which functions as an electrode for a contact with the skin of the hand to which the device is attached. An electrically conductive outer structure functions as an electrode for a contact with the user's other hand and it is electrically isolated from the electrically conductive inner structure. The electrically conductive outer structure on the measuring device extends at least to opposite sides of the hand to which the device is attached, and at least part of the electrically conductive outer surface is on the outer surface of the measuring device, on opposite sides of the hand to which the device is attached. The electrically conductive outer structure and inner structure are connected to a measuring unit for heart rate measurement.

16 Claims, 5 Drawing Sheets

METHOD AND DEVICE FOR MEASURING HEART RATE, AND METHOD FOR MANUFACTURING THE DEVICE

CROSS-REFERENCE TO RELATED APPLICATION

This application claims priority based on Finnish Patent Application No. 20030598, filed on Apr. 17, 2003.

FIELD OF THE INVENTION

The invention relates to a measuring device and a measuring method arranged to measure non-invasively the heart function of a user on whose hand the measuring device has been attached.

BRIEF DESCRIPTION OF THE RELATED ART

Heart rate measurement is based on monitoring the function of the heart. When the heart contracts it causes a series of electric impulses that can be measured in the body. The measurement and analysis of this signal is called electrocardiography (EKG), and the signal itself is known as an EKG signal. Different phases of the heart cycle can be distinguished in the signal.

Heart rate can be measured with a measuring device similar to a wristwatch, for example, the device measuring an EKG signal from the user's hands. The measuring device comprises a measuring unit that may contain for example an electronic signal processing unit for processing the EKG signal, a display, a user interface, and a wristband portion for attaching the measuring device to the user's hand. The inner measuring device surface that sets against the hand is provided with one or more electrodes, each one of which is in contact with the skin and connected to the signal processing unit of the measuring unit. The measuring unit further comprises a second electrode on the outer surface of the measuring device. This electrode is also connected to the signal processing unit, and to produce a contact with the electrode, the user must touch it with one finger of his/her other hand. With each hand thus in contact with a separate electrode, the signal processing unit is capable of measuring and processing the EKG signal transmitted by the electrodes.

However, this kind of measurement involves a number of problems. When the measuring device is touched with one hand, also the hand to which the measuring device is attached is pressed. The forces acting between the hands thus vary considerably, particularly during motion, which impairs the measurement contact, the quality of the detected EKG signal, and thereby also the measurement result. Moreover, it is difficult to keep the finger on the small electrode of the measuring device, and occasionally the contact may be lost, which further impairs the measurement and may even cause it to fail. A lateral hand movement in particular causes motion-related disturbance in a signal.

SUMMARY OF THE INVENTION

It is an object of the invention to provide an improved measuring device, a manufacturing method thereof, and a measuring method to allow a more reliable measuring device and measuring to be obtained.

This is achieved by a heart rate measuring device to be attached around a user's hand, the device comprising: attaching means which are fixed to the measuring unit; an inner surface arranged to be in contact with the skin of the hand to which the device is attached; an outer surface, i.e. a surface other than the inner surface; an electrically conductive inner structure provided on the inner surface of the measuring device and functioning as an electrode for a contact with the skin of the hand to which the device is attached; an electrically conductive outer structure functioning as an electrode for a contact with the user's other hand and electrically isolated from the electrically conductive inner structure; a measuring unit to which the electrically conductive outer structure and inner structure are connected for heart rate measurement. The device is characterized in that: the electrically conductive outer structure of the measuring device extends at least to opposite sides of the hand to which the device is attached; the electrically conductive outer structure comprises at least one electrode on the outer surface of the measuring device, on opposite sides of the hand to which the measuring device is attached, which at least one electrode the user is to touch with separate fingers of his/her other hand from opposite directions of the hand to which the device is attached; and the at least one electrode is connected to the measuring unit with a wire inside the wristband.

The invention further relates to a method for manufacturing a heart rate measuring device to be attached around a user's hand with attaching means which are fixed to the measuring unit; the method comprising: providing an electrically conductive inner structure on an inner surface of the measuring device, the inner surface being in contact with the skin of the hand to which the device is attached and at least part of the electrically conductive inner structure being meant to function as an electrode for the skin contact with the hand to which the device is attached; providing an electrically conductive outer structure on an outer surface of the measuring device to provide an electrode for a contact with the user's other hand, the electrically conductive outer structure being electrically isolated from the electrically conductive inner structure, the outer surface referring to a measuring device surface other than the inner surface; providing a measuring unit with signal processing means; and connecting the electrically conductive outer structure and inner structure to the signal processing means of the measuring unit for heart rate measurement. The method further comprises: producing at least one electrode of the electrically conductive outer structure on the outer surface of the measuring device, on opposite sides of the hand to which the device is attached; and connecting the electrode to the measuring unit with a wire inside the wristband.

The invention still further relates to a method for measuring heart rate, in which method a measuring device is attached around a user's hand, the method comprising: bringing the user's hand to which the measuring device is attached into contact with an electrically conductive inner structure provided on an inner surface of the measuring device that sets against the skin of the hand to which the device is attached; bringing the user's other hand into contact with the device as the user touches with his/her other hand an electrically conductive outer structure provided on the outer surface of the measuring device on the hand to which it is attached, the outer surface referring to a measuring device surface other than the inner surface; and connecting heart rate from the separate hands of the user via the electrically conductive outer structure and inner structure to the measuring unit for heart rate measurement. The method further comprises: bringing the user's other hand into contact with the device by having the user touch with the fingers of his/her other hand at least one electrode of the electrically conductive outer structure on the outer surface of the measuring device and on opposite sides of the hand to which the device is attached, the electrode being connected to the measuring unit with a wire inside the wristband.

Preferred embodiments of the invention are disclosed in the dependent claims.

The invention is based on providing a measuring device with an electrically conductive outer surface for heart rate measurement on opposite sides of a hand to which the device is attached. This enables a firm and convenient grip to be taken both of the measuring device and the hand to which it is attached.

The solution of the invention provides a number of advantages. The contact made by both hands becomes reliable and contact impedance is reduced, due to increased contact surface between the measuring device and the skin as a result of an increase in the number of electrodes or in their surface. Also in demanding measuring conditions, the hold of the other hand from the measuring device and the electrodes can be made strong, firm and, as regards the contact force, more uniform. The electrodes are subjected to forces acting from opposite directions, which considerably reduces contact disturbance caused to the electrodes by the movement of the hands, because a decrease in contact force on one side increases contact force on the other side. This way also the reliability of the heart rate measurement is improved.

BRIEF DESCRIPTION OF THE DRAWINGS

In the following the invention will be described in greater detail with reference to the preferred embodiments and the accompanying drawings, in which.

DETAILED DESCRIPTION OF THE PREFERRED EMBODIMENTS

Figure 1:
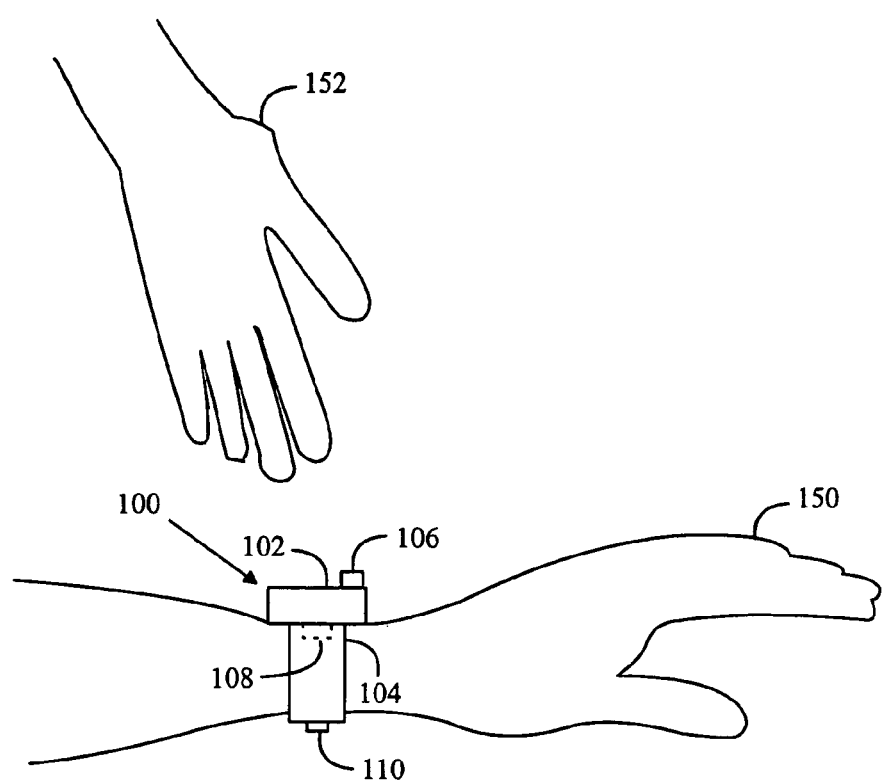
FIG. 1 illustrates a heart rate monitor of the invention to be attached around a hand.

The disclosed solution will be first examined with reference to FIG. 1. A measuring device 100 is attached to a user's hand 150 in the same way as a wristwatch. The measuring device 100 is usually attached to the wrist, although the exact position of the device on the hand is not relevant to the disclosed solution, only the fact that the measuring device 100 can be attached to one of the user's hands 150. The measuring device 100 of the disclosed solution comprises a measuring unit 102 and attaching means 104. The attaching means 104 with which the measuring device 100 is attached to the user's arm may be similar to the wristbands of wristwatches. The measuring unit 102 is usually a heart rate monitor or a wrist computer and it comprises a casing containing for example signal processing means for electric processing of signals, a display for displaying information, and a user interface (these being not shown in FIG. 1). The measuring device has electrodes 106 and 110 on opposite sides of the hand 150 to which the device is attached. In FIG. 1 electrode 106 provided on the outer surface of the measuring device is arranged on the measuring unit 102 and meant for contact by the user's other hand 152. Electrode 108, arranged on the inner surface of the measuring device 102 in FIG. 1, is in turn meant for contact with the skin of the hands 150 to which the measuring device is attached. Electrodes 106 and 108 are electrically isolated from one another.

Figure 2A:
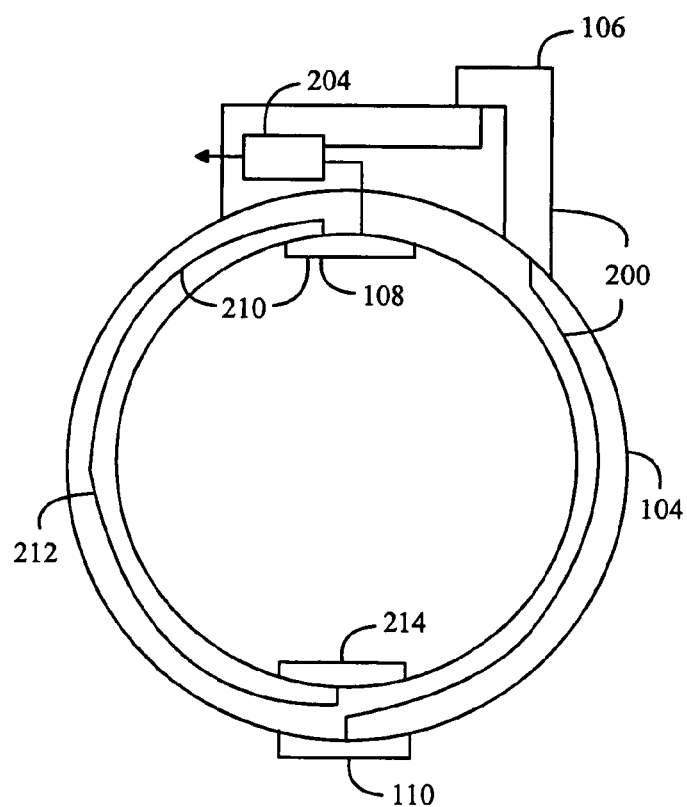
FIG. 2A is a side view of a plane figure of a measuring device.
Figure 2B:
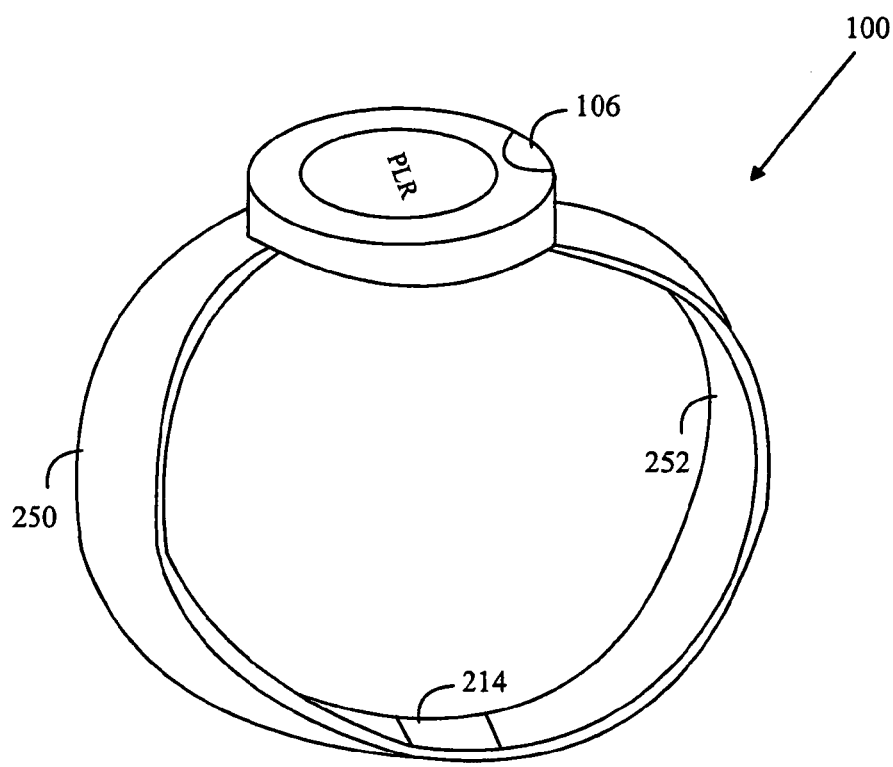
FIG. 2B is a three dimensional view of the measuring device.

Next, the disclosed solution will be examined in greater detail with reference to FIGS. 2A and 2B. The measuring device 100 comprises an electrically conductive outer structure 200 connected to signal processing means 204 of the measuring unit 102. The electrically conductive structure 200 produced on the outer surface of the device may form, for example, at least one electrode 110 which may cover a large part of the outer surface. The outer surface may also comprise at least two electrodes 106, 110, which do not necessarily cover the outer surface as a whole but, instead, the electrodes 106, 110 may form areas separated from each other by an insulating outer surface. The electrically conductive outer structure 200 may, however, comprise a wire 202 inside the wristband 104. The wire 202, which may be a proper electrical wire or a wire made of some other kind of electrically conductive material, such as a conductive polymer, may connect electrode 110 to the measuring device. The wire 202 may also be used to connect electrode 106 to electrode 110, electrodes 110 and 106 being on opposite sides of the hand to which the measuring device is attached. The wire 202 is coupled to the signal processing means 204. The measuring device of the disclosed solution further comprises an electrically conductive inner structure 210, which is also connected to the signal processing means 204. The conductive inner surface 210 may also comprise a number of separate electrodes 108, 214. Thus the inner surface 210 may comprise at least one electrode 214 coupled to the processing means 204 with a wire 212 inside the wristband 104. When at least two electrodes 108, 214 are involved, the electrodes 108, 214 may be coupled together and to the processing means 204 with the wire 212 inside the wristband 104 similarly as in the case of the outer conductive surface 200. The wire 212 may be a proper electrical wire or a wire made of some other kind of electrically conductive material, such as a conductive polymer.

The signal processing means 204 measure heart rate from signals received from the outer and inner structure, and from the signal processing means 204 a measured signal can then be supplied in a wireless or wired transmission to a computer, for example. The signal processing means 204 can be implemented using separate logic components or one or more ASIC circuits (Application Specific Integrated Circuit), for example.

Without the connection established via the skin and the signal processing means 204, there is no galvanic contact between the electrically conductive outer structure 200 and inner structure 210, but they are electrically isolated or separated from one another by a weakly conductive material (having an impedance greater than the impedance between the skin and the electrodes). They may be separated by plastic or some other electrically isolating or weakly conductive material of the wristband 104 and the measuring unit 102. In addition to or instead of the electrode 108 that is in the inner structure 210, under the measuring unit 102, the measuring device 100 may comprise electrode 214 that belongs to the inner structure 210 coupled to the signal processing means through a wire that also belongs to the inner structure 210. If electrode 108, coupled to the signal processing means 204 of the measuring unit 102, is used, electrode 214 may be coupled to electrode 108 by the wire 212. Electrode 214 reduces contact impedance between the hand and the measuring device.

FIG. 2B illustrates the same implementation alternative as FIG. 2A. In the disclosed solution at least part of the electrically conductive outer structure 200 meant for contact with the other hand is located, as indicated by its name, on the outer surface 250 of the measuring device 100. The part of the electrically conductive outer structure 200 on the outer surface 250 of the measuring device may form one or more electrodes. Examples of these are electrode 106 and electrode 110 (not shown in FIG. 2B). The outer surface 250 may be considered to refer to the entire surface of the measuring device 100, apart from the surface that comes into contact with the hand to which the device is attached. Similarly, at least part of the electrically conductive inner structure meant for contact with the hand to which the device is attached is located, as indicated by its name, on the inner surface 252 of the measuring device, the inner surface referring to the measuring device 100 surface that is in contact with the skin of the hand to which the device is attached. The part of the electrically conductive inner structure is electrode 214 (and/or electrode 108, which is not shown in FIG. 2B), for example.

Figure 3A:
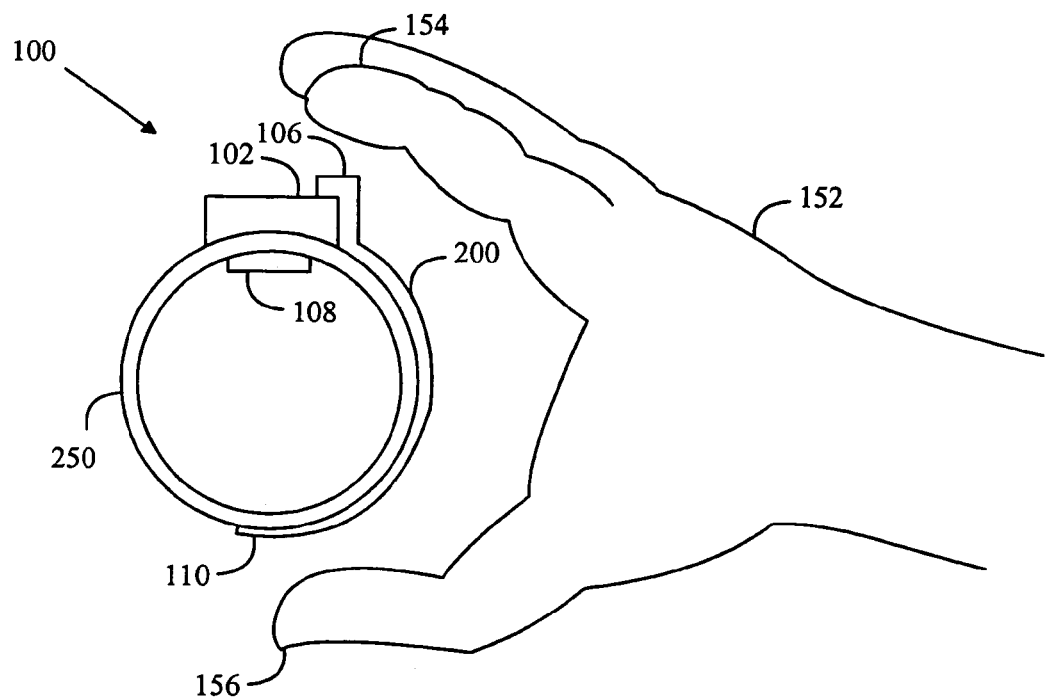
FIG. 3A illustrates an implementation of an outer electrode forming a semi-circle that extends from the upper side of the hand to which the device is attached to the underside thereof.

FIG. 3A shows one of many methods of implementing an electrically conductive structure. According to this alternative, the entire electrically conductive outer structure 200 is arranged on the outer surface 250 of the annular measuring device 100 in the form of a semi-circle, which allows the electrically conductive outer structure 200 as a whole to function as an electrode for the user's other hand 152. In the disclosed solution fingers of the other hand 152 are used for taking a pinch grip of the measuring device 100 such that the hand to which the device is attached is left between the fingers, for example the forefinger 154 and the thumb 156. The forefinger 156, for example, touches one end of the electrically conductive outer structure representing electrode 110, while the thumb touches the other end of the electrically conductive outer structure representing electrode 106.

Figure 3B:
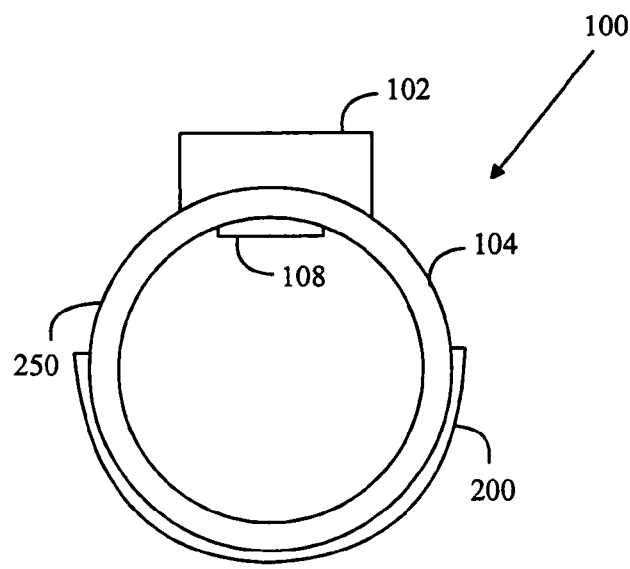
FIG. 3B illustrates an implementation of an outer electrode forming a semi-circle that extends from one side of the hand to which the device is attached to the other side thereof.

The electrically conductive, semi-circular outer structure 200 can be arranged on the outer surface 250 of the measuring device also in the manner shown in FIG. 3B. In this solution the electrically conductive outer structure 200 is not on the measuring unit 102 at all, but entirely on the wristband, which is why there is no need to touch the measuring unit 102 with the fingers of the other hand. The display on the measuring unit 102 of the measuring device 100 can thus be viewed without the other hand disturbing visibility. Instead of a semi-circle, the electrically conductive outer structure 200 may be arranged in the form of a longer portion on the outer surface 250 of the measuring device 100. An electrically conductive structure 200 slightly smaller than a semi-circle is also possible, but according to the disclosed solution it must be possible to take a pinch grip of the measuring device 100 with the fingers of the other hand so that the hand to which the device is attached is left between the fingers that touch the electrically conductive outer structure 200, and the contact force applied through the fingers on parts of the electrically conductive outer structure 200 presses these parts towards each other. This kind of situation appears when the electrically conductive outer structure 200 on the measuring device 100 extends to opposite sides of the hand to which the device is attached and when at least portions of the structure that are on opposite sides of the hand to which the measuring device 100 is attached are arranged on the outer surface of the measuring device.

Figure 4A:
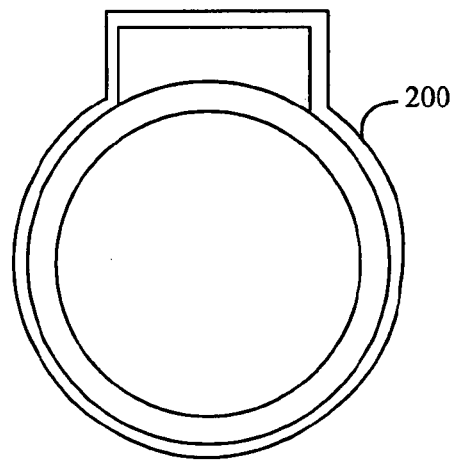
FIG. 4A is a side view of a measuring device, illustrating an outer electrode implemented on the entire outer surface of the device.
Figure 4B:
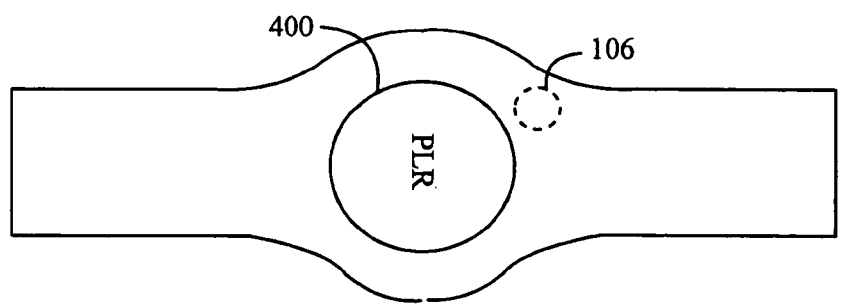
FIG. 4B is a top view of a measuring device, illustrating an outer electrode implemented on the entire outer surface of the device.

FIG. 4A shows one of many methods of implementing the electrically conductive structure. In this solution the electrically conductive outer structure 200 extends in a circular manner around the entire measuring device 100, on the outer surface thereof. FIG. 4B illustrates the solution of FIG. 4A by showing the measuring device of FIG. 4A from above. The measuring device 100 may be entirely covered with the electrically conductive outer structure. However, the display 400, for example, is not necessarily coated with the electrically conductive outer structure 200, for example, although it is possible to produce a transparent layer made of an electrically conductive material (an Indium-Tin-Oxide, or ITO, layer) onto the display 400.

Figure 5:
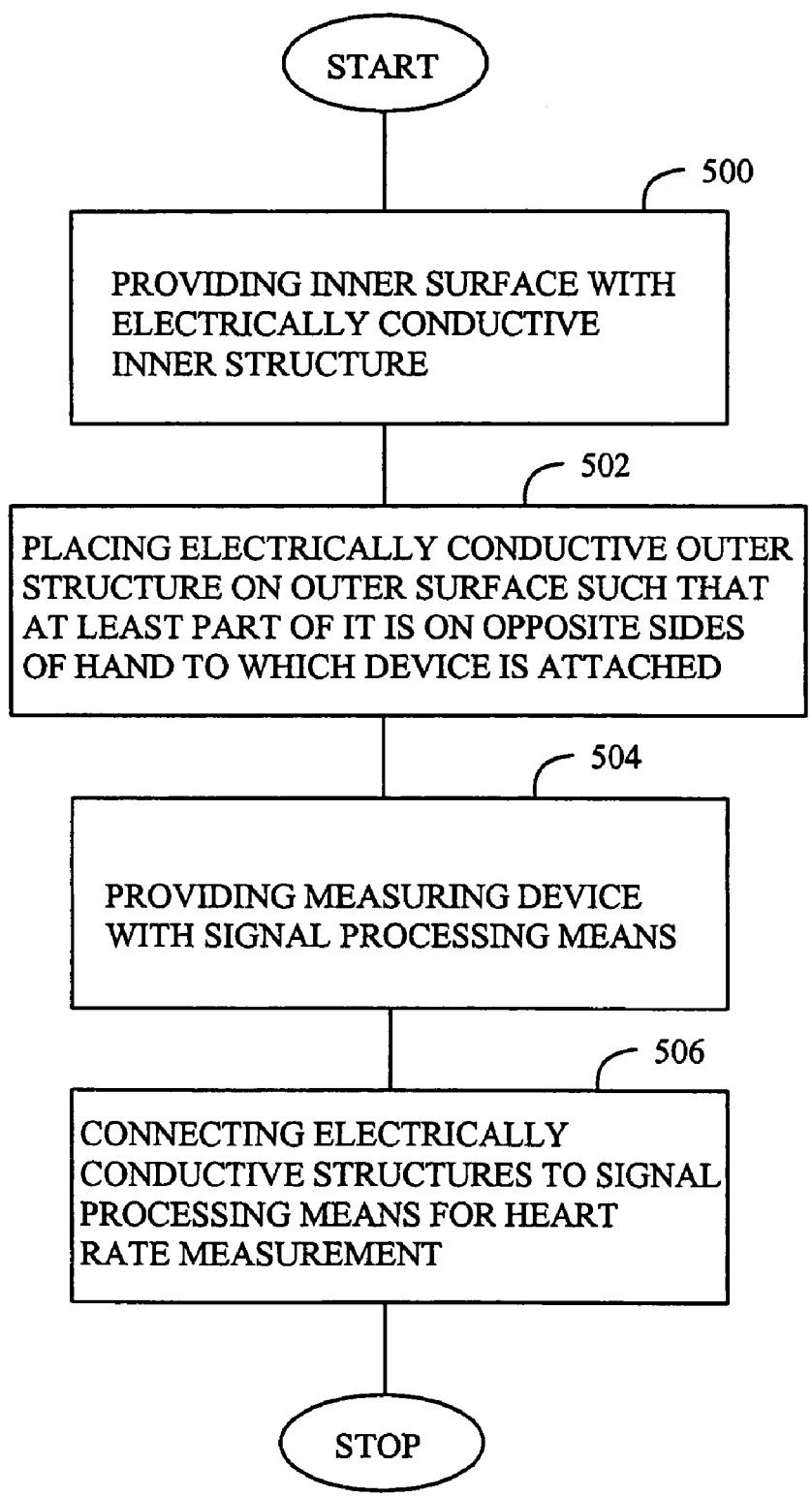
FIG. 5 is a flow diagram of a method for manufacturing the measuring device.

Finally, with reference to FIGS. 5 and 6 and to some of the subject matter already discussed, the manufacture of a measuring device and the measurement of heart rate with the device will be discussed. FIG. 5 is a flow diagram illustrating a method for manufacturing the measuring device. In step 500 the electrically conductive inner structure is placed on the inner surface of the measuring device. In step 502 the electrically conductive outer structure is arranged to the measuring device in such a way that at least part of the structure is on opposite sides of the hand to which the device is attached. The electrically conductive outer structure and inner structure may be made of electrically conductive plastic or metal. The electrically conductive material may be provided as a coating on the outer and/or inner structure. In step 504 the measuring device is provided with signal processing means. In step 506 the electrically conductive outer structure and inner structure are connected to the signal processing means for heart rate measurement.

Figure 6:
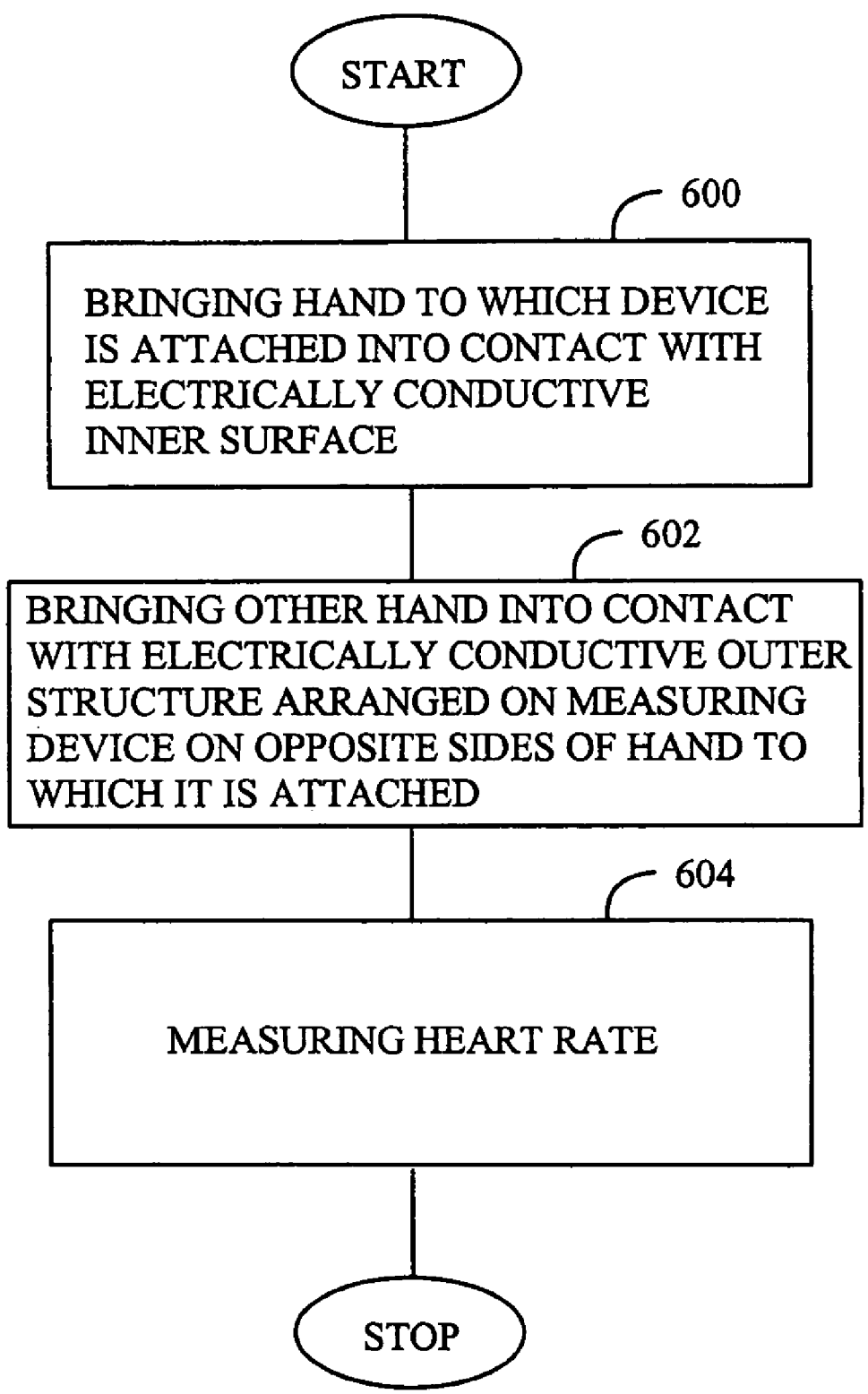
FIG. 6 is a flow diagram of a method for measuring heart rate.

FIG. 6 is a flow diagram of the measurement method. In step 600 the electrically conductive inner structure makes contact with the hand to which the device is attached. In step 602 at least parts of the electrically conductive outer structure make contact with the other hand, these parts being on opposite sides of the hand to which the measuring device is attached. In step 604, heart rate is measured from both hands of the user by means of the electrically conductive outer structure and inner structure. The measurement may be activated for example when the impedance between the electrically conductive outer structure and inner structure is less than one megohm due to the electrical conductivity of the skin between the skin contacts. Another way to ensure that the measurement is activated is to use a pressure-sensitive PVDF (polyvinylidenefluoride) film in the electrically conductive outer structure (and/or inner structure) at the locations brought into contact with the hand. The PVDF film transmits to the measuring unit an electric signal corresponding to the applied pressure and when the pressure exceeds a predetermined threshold value, a conclusion can be made that a sufficiently good contact has been created between the hands and the measuring device. Instead of this activation mechanism, the device may be activated by a mechanic switch. Measurement of heart rate in the measuring unit may be based on detecting, in manner known per se, an R peak of a QRS complex appearing in the signal, or on identifying the QRS complex in an EKG signal by means of a matched filter. The letters Q, R, and S in the QRS complex refer to potential phases, known per se, appearing in the functioning of the heart.

Although the invention is disclosed above with reference to examples illustrated in the accompanying drawings, it is apparent that the invention is not restricted thereto, but can be varied in many ways within the scope of the appended claims.

What is claimed is:

1. A heart rate measuring device to be attached around a user's wrist, the device comprising:
    an attachment device fixed to a measuring unit;
    an inner surface arranged to be in contact with skin of the wrist to which the device is attached;
    an outer surface other than the inner surface;
    an electrically conductive inner structure provided on the inner surface of the measuring device and comprising at least one electrode adapted to be in contact with the skin of the wrist to which the device is attached;
    an electrically conductive outer structure comprising at least one electrode adapted to be in contact with the user's other hand and electrically isolated from the electrically conductive inner structure;
    a measuring unit to which the electrically conductive outer structure and inner structure are connected for heart rate measurement, wherein
    the electrically conductive outer structure of the measuring device extends at least to opposite sides of the wrist to which the device is attached, the electrically conductive outer structure comprises at least a first electrode and a second electrode on the outer surface of the measuring device, on opposite sides of the wrist to which the measuring device is attached, which first electrode and second electrode the user is to touch with separate fingers of the user's other hand from opposite directions of the wrist to which the device is attached, wherein the electrically conductive outer structure comprises at least two electrodes, which are on different sides of the wrist to which the device is attached, and
    at least one of the electrodes being connected to the measuring unit with a wire inside the wristband.

2. A measuring device according to claim 1, wherein the electrically conductive outer structure forms a uniform electrode on the outer surface of the measuring device, which electrode the user is to touch with separate fingers of the user's other hand at least from opposite directions in relation to the wrist to which the device is attached.

3. A measuring device according to claim 1, wherein the electrically conductive outer structure forms a uniform electrode extending on part of the outer surface of the measuring device to opposite sides of the wrist to which the device is attached, which electrode the user is to touch with separate fingers of the user's other hand at least from opposite directions in relation to the wrist to which the device is attached.

4. A measuring device according to claim 1, wherein the electrically conductive outer structure comprises at least two electrodes which are connected together with a wire inside the wristband.

5. A measuring device according to claim 1, wherein the electrically conductive outer structure is made of electrically conductive plastic.

6. A measuring device according to claim 1, wherein the electrically conductive outer structure is made of electrically conductive metal.

7. A heart rate measuring device to be attached around a user's wrist, the device comprising:
    an attachment device fixed to a measuring unit;
    an inner surface arranged to be in contact with skin of the wrist to which the device is attached;
    an outer surface other than the inner surface;
    an electrically conductive inner structure provided on the inner surface of the measuring device and comprising at least one electrode adapted to be in contact with the skin of the wrist to which the device is attached;
    an electrically conductive outer structure comprising at least one electrode adapted to be in contact with the user's other hand and electrically isolated from the electrically conductive inner structure;
    a measuring unit to which the electrically conductive outer structure and inner structure are connected for heart rate measurement, wherein
    the electrically conductive outer structure of the measuring device extends at least to opposite sides of the wrist to which the device is attached, the electrically conductive outer structure comprises at least a first electrode and a second electrode on the outer surface of the measuring device, on opposite sides of the wrist to which the measuring device is attached, which first electrode and second electrode the user is to touch with separate fingers of the user's other hand from opposite directions of the wrist to which the device is attached, wherein the electrically conductive inner structure comprises at least two electrodes on the inner surface of the measuring device and on different sides of the wrist to which the device is attached; and
    at least one of the electrodes being connected to the measuring unit with a wire inside the wristband.

8. A measuring device according to claim 7, wherein the electrically conductive outer structure forms a uniform electrode on the outer surface of the measuring device, which electrode the user is to touch with separate fingers of the user's other hand at least from opposite directions in relation to the wrist to which the device is attached.

9. A measuring device according to claim 7, wherein the electrically conductive outer structure forms a uniform electrode extending on part of the outer surface of the measuring device to opposite sides of the wrist to which the device is attached, which electrode the user is to touch with separate fingers of the user's other hand at least from opposite directions in relation to the wrist to which the device is attached.

10. A measuring device according to claim 7, wherein the electrically conductive outer structure comprises at least two electrodes which are connected together with a wire inside the wristband.

11. A measuring device according to claim 7, wherein the electrically conductive outer structure is made of electrically conductive plastic.

12. A measuring device according to claim 7, wherein the electrically conductive outer structure is made of electrically conductive metal.

13. A method for manufacturing a heart rate measuring device to be attached around a user's wrist with an attachment device fixed to a measuring unit, the method comprising:
    providing an electrically conductive inner structure on an inner surface of the measuring device, the inner surface being in contact with skin of the wrist to which the device is attached and at least part of the electrically conductive inner structure being adapted to function as an electrode adapted to be in contact with skin of the wrist to which the device is attached;

providing an electrically conductive outer structure on an outer surface of the measuring device to provide a first electrode and a second electrode adapted to be in contact with the user's other hand, the electrically conductive outer structure being electrically isolated from the electrically conductive inner structure, the outer surface being a measuring device surface other than the inner surface;

providing a measuring unit comprising a signal processing device; and connecting the electrically conductive outer structure and inner structure to the signal processing device of the measuring unit for heart rate measurement, the method further comprising:

producing at least one electrode of the electrically conductive outer structure on the outer surface of the measuring device, on opposite sides of the wrist to which the device is attached, wherein the electrically conductive outer structure comprises at least two electrodes, which are on different sides of the wrist to which the device is attached; and connecting at least one of the electrodes to the measuring unit with a wire inside the wristband.

14. A method for measuring heart rate, in which method a measuring device is attached around a user's wrist, the method comprising:

bringing the user's wrist to which the measuring device is attached into contact with an electrically conductive inner structure provided on an inner surface of the measuring device that sets against skin of the wrist to which the device is attached;

bringing the user's other hand into contact with an electrically conductive outer structure provided on an outer surface of the measuring device on the wrist to which the measuring device is attached, the outer surface being a measuring device surface other than the inner surface; and connecting a heart rate signal from the user via the electrically conductive outer structure and inner structure to the measuring unit for heart rate measurement, the method further comprising:

bringing the user's other hand into contact with the device by having the user touch with the fingers of the user's other hand at least a first electrode and a second electrode of the electrically conductive outer structure on the outer surface of the measuring device and on opposite sides of the wrist to which the device is attached, at least one of the electrodes being connected to the measuring unit with a wire inside the wristband, wherein the electrically conductive outer structure comprises at least two electrodes, which are on different sides of the wrist to which the device is attached.

15. A method for manufacturing a heart rate measuring device to be attached around a user's wrist with an attachment device fixed to a measuring unit, the method comprising:

providing an electrically conductive inner structure on an inner surface of the measuring device, the inner surface being in contact with skin of the wrist to which the device is attached and at least part of the electrically conductive inner structure being adapted to function as an electrode adapted to be in contact with skin of the wrist to which the device is attached;

providing an electrically conductive outer structure on an outer surface of the measuring device to provide a first electrode and a second electrode adapted to be in contact with the user's other hand, the electrically conductive outer structure being electrically isolated from the electrically conductive inner structure, the outer surface being a measuring device surface other than the inner surface;

providing a measuring unit comprising a signal processing device; and connecting the electrically conductive outer structure and inner structure to the signal processing device of the measuring unit for heart rate measurement, the method further comprising:

producing at least one electrode of the electrically conductive outer structure on the outer surface of the measuring device, on opposite sides of the wrist to which the device is attached, wherein the electrically conductive inner structure comprises at least two electrodes on the inner surface of the measuring device and on different sides of the wrist to which the device is attached; and connecting at least one of the electrodes to the measuring unit with a wire inside the wristband.

16. A method for measuring heart rate, in which method a measuring device is attached around a user's wrist, the method comprising:

bringing the user's wrist to which the measuring device is attached into contact with an electrically conductive inner structure provided on an inner surface of the measuring device that sets against skin of the wrist to which the device is attached;

bringing the user's other hand into contact with an electrically conductive outer structure provided on an outer surface of the measuring device on the wrist to which the measuring device is attached, the outer surface being a measuring device surface other than the inner surface; and connecting a heart rate signal from the user via the electrically conductive outer structure and inner structure to the measuring unit for heart rate measurement, the method further comprising:

bringing the user's other hand into contact with the device by having the user touch with the fingers of the user's other hand at least a first electrode and a second electrode of the electrically conductive outer structure on the outer surface of the measuring device and on opposite sides of the wrist to which the device is attached, at least one of the electrodes being connected to the measuring unit with a wire inside the wristband, wherein the electrically conductive inner structure comprises at least two electrodes on the inner surface of the measuring device and on different sides of the wrist to which the device is attached.

* * * * *